United States Patent [19]

Janerette

[11] Patent Number: 5,178,642
[45] Date of Patent: Jan. 12, 1993

[54] INOCULUM FROM ECTOMYCORRHIZAL FUNGI FORMING ENDOMYCORRHIZAL INFECTION WITH HERBACEOUS PLANTS

[76] Inventor: Carol A. Janerette, 2218 Dickens Terr., Newark, Del. 19702

[21] Appl. No.: 725,392

[22] Filed: Jun. 28, 1991

Related U.S. Application Data

[63] Continuation of Ser. No. 385,515, Jul. 27, 1989, abandoned, which is a continuation-in-part of Ser. No. 83,474, Aug. 10, 1987, abandoned.

[51] Int. Cl.$^5$ .................. A01G 1/00; A01N 63/00; C12N 1/14
[52] U.S. Cl. .................. 47/58; 424/93 N; 424/93 Q; 435/254; 435/911
[58] Field of Search .................. 47/1.1, 58; 800/200; 435/254, 520, 911, 176; 71/5, 6, 7, 59; 424/93 Q, 93 M, 93 N, 93 R

[56] References Cited

U.S. PATENT DOCUMENTS

| | | | |
|---|---|---|---|
| 2,813,821 | 11/1957 | Updegraff et al. | 195/116 |
| 3,580,811 | 5/1971 | Hidy et al. | 435/911 |
| 4,294,037 | 10/1981 | Mosse et al. | 47/59 |
| 4,327,181 | 4/1982 | Litchfield et al. | 435/176 |
| 4,551,165 | 11/1985 | Warner | 71/24 |
| 4,594,809 | 6/1986 | Ower et al. | 47/1.1 |
| 4,599,312 | 7/1986 | Mugnier et al. | 435/172.3 |

FOREIGN PATENT DOCUMENTS

| | | | |
|---|---|---|---|
| 209627 | 1/1987 | European Pat. Off. | 47/1.1 |
| 2071058 | 9/1971 | France | 47/1.1 |

OTHER PUBLICATIONS

"Ectomycorrhiza Formation in Eucalyptus: I. Pure Culture Malajczuk N. et al., Synthesis, Host Specificity and Mycorrhizal Compatibility with *Pinus radiata*", 92 *The New Rhytologist*, (1982), pp. 467–482.
Harley, J. L., (1972) *The Biology of Mycorrhiza*, 2nd ed., Leonard Hall, p. 79.
Moore-Landecker, E. (1982) "Aeration" *Fundamentals of the Fungi*, Prentice-Hall, Inc., Englewood Cliffs, N.J., pp. 304 and 305.
Malloch, D. (1981), "Special Techniques" *Moulds: Their Isolation, Cultivation and Identification* Univ. of Toronto Press, Toronto pp. 38 and 39.
Alexopoulos, C. et al. (1979) "Mycorrhizal" *Introductory Mycology* 3rd ed., John Wiley and Sons, New York, pp. 450–452.
Daniels, B. A. et al., (1981) "Evaluation of the Commercial Value of the Vesicular-Arbuscular Mycorrhizal Fungus *Glomus epigaeus*" *New Phytol*, vol. 87, pp. 345–354.
Crush, J. R., et al. (1975) "Preliminary Results on the Production of Vesicular-Arbuscular-Mycorrhizal Inoculum by Freeze Drying" (Sanders et al. Ed.) *Rothamsted Exper. Sta.*, Harpenden, U.K. pp. 485–493.
Piché, Y. et al. (1982) "Development of Mycorrhizae Extramatrical Myceliumand Sclerotia on *Pinus Strobus* Seedlings" *New Phytol*, vol. 92, pp. 128–137.
Daniels Hetrick, B. A. (1984) "Spore Germination and In Vitro Culture of Vesicular-Arbuscular Mycorrhizal Fungi", *Applications in Mycorrhizal Fungi in Crop Production*, Univ. of Fla., pp. 17–22.
Hile, N., et al. (1969) "*In Vitro* Culture of *Pisolithus tinctorius* Myceluim" *Mycologia* 61, pp. 195–198.
Marks, D. H., (1975) "Mycorrhizal and Establishment of Freeson Stripmined Land" *The Ohio Journal of Sciences* vol. 75, No. 6, pp. 288–297.
Marx, D. H. (1980) "Role of Mycorrhizae in Forestation of Surface Mines" *Proc. Trees for Redamation*, pp. 109–116.
Marks, G. C., et al. (1972) "Structure, Morphogenesis and Ultrastructure of Ectomycorrhizal" In *Ectomycorrhizal Their Ecology and Physiology* (Marks, G. C., ed.) Academic Press Inc., New York, pp. 2–35.
Ruehle, J. L., et al., (1979) "Fiber, Food, Fuel, and Fungal Symbionts" *Science*, vol. 206, pp. 419–422.
Tinker, P. B. H., (1975) *Proc. of the 29th Symposium of the Soc. of Experimental Biology*, pp. 325–349.
Snell and Dick, "A Glossary of Mycology", Cover page & pp. 96 & 193, Harvard U. Press (1957).
Marx, "Growth and Ectomycorrhizal Development of Loblolly Pine Seedlings in Fumigated Soil Infested with the Fungal Symbiont Pisolithus Tinctorius", Forest Science, vol. 22, No. 3, pp. 245–254 (1975).
Watrud, "Methods and Principles of Mycorrhizal Research", p. 81, The American Phytopathological Society (1982).
Hudson, "Fungal Biology", pp. 218–219 (1986).
Smith & Douglas, "The Biology of Symbiosis", pp. 152–153 (1987).

*Primary Examiner*—James R. Feyrer
*Attorney, Agent, or Firm*—Darby & Darby

[57] ABSTRACT

Fungal inoculants for plants producing ectomycorrhizae with woody plants or endomycorrhizae with leafy plants are formed in perlite from microsclerotia-producing fungi such as *Cenococcum geophilium*.

16 Claims, No Drawings

INOCULUM FROM ECTOMYCORRHIZAL FUNGI FORMING ENDOMYCORRHIZAL INFECTION WITH HERBACEOUS PLANTS

This application is a continuation of Ser. No. 07/385,515, filed Jul. 27, 1989, now abandoned, which, in turn, was a continuation-in-part of Ser. No. 07/083,474, filed Aug. 10, 1987, now abandoned.

BACKGROUND OF THE INVENTION

1. Field of the Invention

This invention relates to mycology, more specifically, to a process for the production of inoculants for herbaceous plants and to the inoculants so produced.

2. Prior Art

As noted above, this invention relates to mycology, and the momenclature used is intended to be consistent with Snell and Dick, A Glossary of Mycology, Harvard U. Press, Cambridge, Mass. (1957).

Mycorrhizae are symbiotic associations between the hyphae of certain fungi and the absorbing organs-typically the roots of plants. They are classified according to the manner in which the fungus infects the root. The two main types are ectomycorrhizae in which fungal hyphae penetrate the intercellular spaces between root cells without entering the interior of the cells, and endomycorrhizae where projections of the fungus enter the interior of the cell.

Ectomycorrhizae are generally associated with trees and other woody species and are formed by "higher fungi" that are found in a number of families of basidiomycetes and ascomycetes. In ectomycorrhizae, the normal branching pattern in the roots is changed. Roots infected with ectomycorrhizal fungi are short, swollen, branched and lack root hairs.

Endomycorrhizae are generally associated with herbaceous plants such as grasses, corn, onions and many more, however there are some trees that also form endomycorrhizae. Endomycorrhizae are formed from spores produced by "lower fungi," classified as zygomycetes, and belong to one family, the Endogonales. The fungi that produce these spores are unknown. From the outside, the infected roots look normal, and the only way to detect the infection is by microscopic examination. Then one can see that the hyphal projections of the fungus have invaded the cells forming small branches (arbuscles) and/or swellings at tips of some hyphae (vessicles). Many endomycorrhizae are called "Vessicular-Arbuscular Mycorrhizae" or VAM, because of the presence of vessicles and arbuscles inside root cells. Ectomycorrhizae do not have vessicles or arbuscles.

Ectomycorrhizal fungal inoculants for woody plants such as pine have been produced. See, for example, Litchfield et al., U.S. Pat. No. 4,327,181, "Aerobic Submerged Fermentation of Sporulating Ectomycorrhizal Fungi" (1982) disclosing liquid culture of selected fungi for broadcast over forest soil. Marx et al., "Growth and Ectomycorrhizal Development of Loblolly Pine Seedlings in Fumigated Soil Infested with the Fungal Symbiont *Pisolithus tinctorium*," Forest Science Vol. 22 No. 3, pp. 245-254 (1975), show the use of *Pisolithus tinctorius* cultured in an agar/vermiculite/peat moss medium in forest nurseries. See also Mosse et al., U.S. Pat. No. 4,294,037, "Production of Mycorrhizal Fungi" (1981) and Warner, U.S. Pat. No. 4,551,165, "Mycorrhizal Seed Pellets" (1985).

As far as known, however, inoculants suitable for leafy plants such as wheat or the common vegetables corn, onion, asparagus and the like have not heretofore been produced. Compare Watrud, "Spore Germination and Axenic Culture of Endomycorrhizae," writing at page 81 of Methods and Principles of Mycorrhizal Research, the American Phytopathological Society (1982): ". . . To date, successful axenic subculture of hyphae of vesicular-arbuscular mycorrhizae has yet to be reported. . . ." See also Hudson, Fungal Biology, pp. 218 and 219, Edward Arnold (1986); Smith and Douglas, The Biology of Symbiosis, pp. 152 and 153, Edward Arnold (1987); and Mugnier et al., U.S. Pat. No. 4,599,312, "Method of Producing Endomycorrhizian Fungi with Arbuscules and Vesicles in Vitro" (1986).

DETAILS OF THE INVENTION

In accordance with the present invention, it has been found that fungal inoculants for herbaceous plants can be made by a versatile process in which (1) mycelia of selected ectomycorrhizal fungi are grown from cultures on a solid medium and (2) mycelia still in the solid medium (fungal plugs) are axenically added to perlite wetted with a nutrient solution and incubated in vitro. After about three months' incubation, the product is an inoculant which can be used (3) either broadcast, e.g., with forest trees (ectomycorrhizal), or axenically or otherwise with leafy plants (endomycorrhizal).

The solid medium used in the growth of mycelia (1) is generally hardened agar. Modess Modification of Hagem Agar in the agar can be the nutrient. Other nutrients, such as a modified Melin and Rama Das Agar, can also be used. Three or four weeks in the dark at around 25° C. provide sufficient time for growth.

Fungal plugs taken from the agar growth medium are (2) axenically added to jars containing perlite and nutrient solution and incubated in vitro for about three months in the dark under quiescent and substantially anerobic conditions. In this connection, "quiescent" simply means without agitation and "substantially anerobic" means that air or oxygen need not be supplied to the culture, not that they must be excluded. A useful nutrient solution is Fowells and Krauss's pine nutrient solution modified by the addition of glucose and thiamine (Fowells and Krauss, "The inorganic nutrition of Loblolly pine and Virginia pine with special reference to nitrogen and phosphorus" Forest Science 5:95–112 (1959)).

It should be noted that the inert carrier used in the nutrient solution is somewhat selective. The most satisfactory results have been obtained with perlite as an effective carrier although some modified clays can be used. Vermiculite has been found ineffective under the conditions disclosed. The proportion of carrier to liquid nutrient (carrier/nutrient weight ratio) is not critical but around at least 2/1 has been found satisfactory to provide an effective saturated support.

As noted, the inoculum prepared above can be used (3) by broadcast sowing with woody plants in the fashion well known (ectomycorrhizae) or to facilitate the growth of leafy plants (endomycorrhizae). In the latter case, one axenically germinated seed can be placed on top of one teaspoon full of the fungus inoculum about three centimeters below the surface of a flower pot filled with perlite. The plants are then grown in the greenhouse for four months. The pots are saturated twice weekly with a low-phosphorus nutrient solution (Peter's Lo Phos Fertilizer).

Known ectomycorrhizal fungi that formed endomycorrhizal infection with corn, wheat, onion, and/or asparagus plants include the following:

TABLE I

| | Name | Source |
|---|---|---|
| 1. | *Rhizopogon roseolus* (Melhuish #20) | John Melhuish U.S.D.A. Forest Service |
| 2. | *Pisolithus tinctorius* (ATCC #38054) | American Type Culture Collection |
| 3. | *Amanita muscaria* (Melhuish #21) | John Melhuish U.S.D.A. Forest Service |
| 4. | *Astraeus hygrometricus* (ATCC #46449) | American Type Culture Collection |
| 5. | *Cenococcum geophilum* (ATCC #38052) | American Type Culture Collection |
| 6. | *Scleroderma aurantium* (ATCC #58507) | American Type Culture Collection |
| 7. | *Athelia neuhoffii* (Melhuish #47) | John Melhuish U.S.D.A. Forest Service |
| 8. | *Boletinellus merulioides* (Melhuish #64) | John Melhuish U.S.D.A. Forest Service |
| 9. | *Hebeloma anthracophilum* (Melhuish #54) | John Melhuish U.S.D.A. Forest Service |
| 10. | *Hebeloma crustuliniforme* (Melhuish #53) | John Melhuish U.S.D.A. Forest Service |
| 11. | *Paxillus involutus* (ATCC #46218) | American Type Culture Collection |
| 12. | *Piloderma bicolor* (Melhuish #50) | John Melhuish U.S.D.A. Forest Service |
| 13. | *Rhizopogon nigrescens* (Melhuish #38) | John Melhuish U.S.D.A. Forest Service |
| 14. | *Scleroderma albidum* (ATCC #58021) | American Type Culture Collection |
| 15. | *Scleroderma polyrhizum* (Melhuish #68) | John Melhuish U.S.D.A. Forest Service |
| 16. | *Suillus cothurnatus* (Melhuish #31) | John Melhuish U.S.D.A. Forest Service |
| 17. | *Alpova pachyploeus* (Marx #258) | Dr. Donald Marx U.S.D.A. Forest Service |
| 18. | *Boletus punctipes* (Melhuish #15) | John Melhuish U.S.D.A. Forest Service |
| 19. | *Lactarius deliciosus* (ATCC #36647) | American Type Culture Collection |

While the reasons for the efficacy of the present inoculum and its preparation are not completely understood, it can theoretically be explained as follows. Fungi are able to propagate from a number of sources or propagules including spores, infected root fragments, mycelia, hyphae, etc. Another propagule is sclerotia (cf. Willets, "Sclerotium Formation," Filamentous Fungi 3:197-213 (1978)), and this is believed involved here. The sclerotia are too small to be seen by the naked eye but they can be seen with a microscope. Another propagule is denoted "microsclerotia" (cf. Baard et al. "Structure and Lysis of Microsclerotia...," Trans. Br. Mycol. Soc. 77(2):251-260 (1981)). The development of the mycelium in contact with the inert support and nutrient thus proceeds until sclerotia, microsclerotia, or their initials are produced. Operable fungi for the present inventions are, in any event, those fungi which produce sclerotia or microsclerotia. Spores are produced at the same time, and the product, containing fungal hyphae, microsclerotia, spores, sclerotia, or their initials is an inoculum with a good shelf life.

There follow examples illustrating the invention in detail:

EXAMPLES 1-6

A. Preparation of Inoculum

Selected fungi (*Cenococcum geophilum*, *Pisolithus tinctorius*, *Astraeus hygrometricus*, *Amanita muscaria*, *Rhizopogon roseolus*, and *Scleroderma aurantium*) were axenically grown from mycelia for three weeks at 24° C. in the dark in petri plates on Hagem's nutrient agar modified by Modess (Modess, O. 1941. Zur Kenntnis der Mykorrhizabildner von Kiefer und Fichte. Symbolae Bot. Upsalienses 5(1):1-146) as shown in Table II.

TABLE II

| Formulation* of Modess Modification of Hagem Agar | |
|---|---|
| $KH_2PO$ | 0.5 g |
| $MgSO_4 \cdot 7H_2O$ | 0.5 g |
| $NH_4Cl$ | 0.5 g |
| $FeCl_3$ (1% solution) | 1.0 ml |
| Glucose | 5.0 g |
| Malt extract | 5.0 g |
| Agar | 10.0 g |
| $H_2O$ (distilled) | 1000.0 ml |

*Final pH = 4.7

Subsequently, 0.5 mm plugs were cut from the periphery of the fungal colonies and axenically added to separate test tubes containing 40 ml (8 g) of strained perlite and 20 ml of Fowells and Krauss's modified nutrient solution had previously been autoclaved at 120° C. and 15 lbs. pressure for 20 minutes. Inoculated test tubes were incubated for three months in the dark at 24° C.

TABLE III

| Modified Fowells and Krauss's Nutrient Solution Formulation* | |
|---|---|
| $NH_4NO_3$ | 0.68 ml of 1 molar stock solution |
| $KH_2PO_4$ | 0.15 ml of 1 molar stock solution |
| $MgSO_4$ | 0.95 ml of 1 molar stock solution |
| $CaCl_2$ | 0.95 ml of 1 molar stock solution |
| NaCl | 0.95 ml of 1 molar stock solution |
| KCl | 2.92 ml of 1 molar stock solution |
| Ferric Citrate** | 1.10 ml of stock solution |
| Combined minor elements*** | 0.13 ml of stock solution |
| Thiamine | 50 µg (microgram) |
| Glucose | 2.5 g |
| HCl | 1.5 ml of 1N solution |
| $H_2O$ (distilled) | 1000 ml |

*Final pH = 5.7
**Stock Solution of Ferric Citrate:

| Ferric Citrate | 2.5 g |
|---|---|
| Citric Acid | 1.6 g |
| $H_2O$ | 250 ml |

***Stock Solution of Minor Elements:

| $CuSO_4 \cdot 5H_2O$ | 8.0 mg |
|---|---|
| $ZnSO_4 \cdot 4H_2O$ | 21.8 mg |
| $MnCl_2 \cdot 4H_2O$ | 180.0 mg |
| $H_3BO_3$ | 285.5 mg |
| $H_2Mo_4 \cdot H_2O$ | 2.1 mg |
| $H_2O$ | 100 ml |

Five ml of Fowells and Krauss's nutrient solution was added to each test tube and thoroughly mixed with the incubated inoculum before use.

B. Growth of Endomycorrhizal Structures in Leafy Plants

Seeds of onion, wheat, corn and asparagus that had been soaked in distilled water overnight were washed for 1 minute in 1% $HgCl_2$ with 1 ml of Tween 20 per liter and rinsed three times with sterile distilled water. Seeds were then axenically placed in sterile petri plates containing moistened filter paper and allowed to germinate in the dark at 24° C. When emerged radicles were between 1 cm and 3 cm long (within 1 week for all seeds) they were planted in the greenhouse in 4-inch pots filled with strained horticultural grade perlite. A hole was dug 3 cm from the surface, and one teaspoon full of the fungus inoculum was put in the hole with one germinated seed placed on top of the inoculum and covered with perlite. Twenty pots were prepared for each fungus being tested along with twenty control plants of each seed type. Each pot was placed on top of an inverted, empty 5-inch pot to eliminate cross-contamination on the green-house bench. All pots were saturated with the Fowells and Krauss's solution. The pots were watered daily and, in addition, saturated twice a week with Peter's Lo Phos Fertilizer.

Each of the six fungi being tested was used as inoculum for the onion seeds. Only *Cenococcum geophilum* and *Pisolithus tinctorius* were used to inoculate the corn, wheat, and asparagus seeds.

Inoculated plants were grown under normal greenhouse conditions with the day length extended to 12 hours with incandescent light bulbs.

After 8 weeks, plants were periodically removed from the greenhouse and the roots and perlite in which they were grown was examined as follows. Roots were individually washed in distilled water until free of perlite. The perlite that the plant grew in was agitated in 1 liter of distilled water and filtered along with the root washings through one layer of cheesecloth. This filtrate was then refiltered through nested 230 mesh and 325 mesh sieves. The precipitate on the 325 mesh sieve was saved and examined microscopically. The cleaned roots were cleared and stained using the procedure of Kormanik et al. (Kormanik, Bryan and Schultz. "Procedure and equipment for staining large numbers of plant root samples for endomycorrhizal assay." Can. J. Microbiol. 26:536-538 (1980)). This procedure allows the microscopic visualization of fungi and fungal propagules within the intact root.

When roots were examined after 8 weeks in the greenhouse, there was no apparent internal fungal infection in those observed; however, mycelia were present on the exterior of the roots. The perlite washings did reveal the presence of microsclerotia in every instance. When plants were similarly treated for examination after 16 weeks, endomycorrhizal infection was well established in plants treated with all six fungi, and numerous microsclerotia were present on and around the roots. Root samples from plants grown for 16 weeks or more were excised and fixed, dehydrated, and embedded in epoxy resin according to methods in Pizzolato, T. D., 1978, "A tannic acidferric chloride-toluidine blue stain for wood amyloplasts embedded in epoxy resin," Forest Science 24:49-51, and subsequently stained in Alsops reagent for 1 minute at 130° C. by the methods of Alsop (1974) and Pizzolato (1984) (Alsop, D. 1974, "Rapid single solution polychrome and staining of semithin epoxy sections by polyethylene glycol 200 (PEG 200) as a stain solvent," Stain Technology 49:265-272. Pizzolato, T. D. 1984, "Vascular system of the fertile floret of *Anthoxanthum odoratum* L.," Botanical Gazette 145(3):358-371.) The light microscope sections of internal root cells obtained with these procedures revealed the presence of intercellular and intracellular hyphae, vessicles, and spores with all fungi and plants tested. Control plants yielded no evidence of infection or microsclerotia.

An examination of the fungus inocula used to infect the plants showed the presence of numerous sporulating hyphae and spores but no discernable microsclerotia, a situation indicating that microsclerotia initials were present and required more time, plant exudates or both for maturation.

Results of these studies indicate that inocula produced from ectomycorrhizal fungi by procedures outlined above can be used to induce endomycorrhizal infection in herbaceous plants. Furthermore, all the inocula produced were shown to form mycorrhizae with loblolly pine seedlings.

EXAMPLES 7-19

A. Preparation of Inoculum

The preparation of inocula as in Examples 1-16 was substantially repeated except that different fungal species were employed and in a different agar medium.

Selected fungi (*Athelia neuhoffii, Boletinellus merulioides, Hebeloma anthracophilum, Hebeloma crustuliniforme, Paxillus involutus, Piloderma bicolor, Rhizopogon nigrescens, Scleroderma albidum, Scleroderma polyrhizum, Suillus cothurnatus, Alpova pachyploeus, Boletus punctipes,* and *Lactarius deliciosus*) were axenically grown from mycelia for four weeks at 24° C. in the dark in petri plates on a modification of Melin and Rama Das nutrient agar (Melin and Rama Das "Influence of root metabolites on the growth of tree mycorrhizal fungi" Physiol. Plant. 7:851-858 (1954)).

TABLE IV

| Formulation of Modified Melin and Rama Das Agar | |
|---|---|
| $KH_2PO_4$ | 1.0 gm |
| $MgSO_4 \cdot 7H_2O$ | 0.5 gm |
| $NH_4$ Tartrate | 5.0 gm |
| $ZnSO_4$ (1:500) | 0.5 ml |
| Fe Citrate (1%) | 0.5 ml |
| Thiamin | 50.0 µg (microgram) |
| Glucose | 20.0 gm |
| Agar | 10.0 gm |
| Distilled $H_2O$ | to 1000 ml |

Subsequently, 0.5 mm plugs were cut from the periphery of the fungal colonies and two plugs from each fungus were axenically added to a jar containing 100 ml of strained perlite and 55 ml of Fowells and Krauss's modified nutrient solution (Fowells and Krauss. "The inorganic nutrition of loblolly pine and Virginia pine with special reference to nitrogen and phosphorus", For. Sci. 5:95-112)(1959)) as shown above in Table III). The jars containing the perlite and nutrient solution had previously been autoclaved at 120° C. and 15 lbs. pressure for 20 minutes. The inoculated jars were incubated for 3 months in the dark at 24° C.

B. Ectomycorrhizal Infection in Asparagus Plants

Asparagus seeds that had been soaked in distilled water overnight were washed for one minute in 1% $HgCl_2$ with 1 ml of Tween 20 per liter and rinsed three times with sterile distilled water. Seeds were then axenically placed in sterile petri plates containing moistened filter paper and incubated in the dark at 24° C. Six days later, the germinated seeds were planted in 4-inch pots filled with strained horticultural grade perlite. A hole was dug 3 cm from the surface, and one teaspoon full of the fungus inoculum was put in the hole with one germinated seed placed on top of the inoculum and covered with perlite. Ten pots were prepared for each fungus being tested along with twenty control plants. Each pot was placed on top of an inverted empty 5 inch pot to eliminate contamination on the greenhouse bench. All pots were then saturated with the Fowells and Krauss's solution. The pots were watered daily and, in addition, saturated twice a week with Peter's Lo Phos Fertilizer.

Inoculated plants were grown under normal greenhouse conditions. After 4 months, plants were removed from the greenhouse and the roots and perlite in which they were grown was examined as follows: Roots were individually washed in distilled water until free of perlite. The perlite that the plant grew in was agitated in one liter of distilled water and filtered along with the root washings through one layer of cheesecloth. This filtrate was then refiltered through nested 230 mesh and 325 mesh sieves. The precipitate on the 325 mesh sieve was saved and examined microscopically. The cleaned roots were cleared and stained by the procedure of Kormanik et al. (Kormanik, Bryan and Schultz, "Procedure and equipment for staining large numbers of plant root samples for endomycorrhizal assay." Can. J. Microbiol. 26:536–538) (1980). This procedure allows the microscopic visualization of fungi and fungal propagules within the intact root. When plants were examined, endomycorrhizal infection was well established with all of the fungi tested, and numerous microsclerotia were present on and inside the roots.

An examination of the fungus inocula used to infect the plants showed the presence of numerous sporulating hyphae and spores but no discernable microsclerotia were present indicating that microsclerotia initials were present and required more time, plant exudates or both for maturation.

Each of these fungi forms mycorrhizae with Virginia Pine and/or Loblolly Pine in axenic culture.

Results of these studies indicate that inocula produced from ectomycorrhizal fungi by procedures outlined above can be used to induce endomycorrhizal infection in herbaceous plants.

Having described my invention, I claim:

1. A method of growing plants having mycorrhizae associated with their roots comprising the steps of:
    obtaining mycelia of an ectomycorrhizal, microsclerotia-producing fungus,
    contacting propagule of said mycelia with a growth medium containing a particulate carrier and a nutrient solution including sources of nitrogen, potassium, magnesium, ammonia, zinc, sulfur, iron, sugar and thiamine,
    maintaining said contact in the absence of living plant matter in darkness and without aeration for a period of time effective to stress the mycelia, inducing it to produce at least microsclerotia or its initials,
    obtaining an ectomycorrhizal inoculum from said mycelia which is capable of producing intracellular hyphae when contacted with herbaceous plants,
    germinating a seed to produce a seedling,
    infecting said seedling with said inoculum and contacting said seedling with a second nutrient solution, and
    obtaining plants having a symbiotic association with said fungi.

2. The method of claim 1 wherein said seed is of a herbaceous plant and wherein said symbiotic association is of endomycorrhizal morphology.

3. The method of claim 1 wherein the nutrient solution is Fowells and Krauss's pine nutrient solution and the growth medium is pH balanced with acid.

4. A process of producing a mycorrhizal inoculant of a normally ectomycorrhizal fungi for use with either woody or herbaceous plants, comprising the steps of:
    obtaining mycelia of an ectomycorrhizal fungus,
    contacting a propagule of said mycelia with a growth medium containing a particulate carrier and a nutrient solution including sources of carbon, nitrogen, potassium, magnesium, zinc, sulfur and iron, and
    maintaining said contact in the absence of living plant matter in darkness and without aeration for a period of time effective to stress the mycelia, inducing it to produce at least microsclerotia or its initials among said mycelia, and
    obtaining an ectomycorrhizal inoculum containing at least microsclerotia or the initials of microsclerotia, which inoculum is capable of producing intracellular hyphae when contacted with herbaceous plants and; is effective to form mycorrhizal symbiotic associations with the roots of woody plants.

5. The process of claim 4 wherein said maintaining is conducted for about three months at about room temperature.

6. The process of claim 4 wherein said mycelia of ectomycorrhizal fungi are selected from the fungus species consisting of *Rizopogon roseolus, Pisolithus tinctorius, Amanita muscaria, Astraeus hygrometricus, Cenococcum geophilum, Scleroderma aurantium, Athelia neuhoffii, Boletinellus merulioides, Hebeloma anthracophilum, Hebeloma crustuliniforme, Paxillus involutus, Piloderma bicolor, Rhizopogon nigrescens, Scleroderma albidum, Scleroderma polyrhizum, Suillus cothurnatus, Alpova pachyploeus, Boletus punctipes,* and *Lactarius deliciosus.*

7. The process of claim 4 wherein said carrier is selected from the group consisting of perlite and modified clays.

8. The process of claim 7 wherein in said contacting and maintaining steps the weight ratio of said particulate carrier to said growth medium is at least 2:1.

9. The process of claim 8 wherein said carrier is perlite.

10. The process of claim 4 wherein the propagule used in the contacting step are obtained by axenically growing said mycelia in the dark in petri dishes on a nutrient-containing solid second medium.

11. The process of claim 10 wherein the contacting step comprises cutting plugs from said petri dishes on which said mycelia have been grown and axenically contacting the plugs with the growth medium and particulate carrier.

12. The process of claim 11 wherein said carrier is perlite and said solid medium is agar.

13. The method of claim 4 wherein the growth medium is Fowells and Krauss's pine nutrient solution modified by the addition of glucose and thiamine, and pH balanced with acid.

14. A process of producing a mycorrhizal inoculant of a normally ectomycorrhizal fungi for use with either woody or herbaceous plants, comprising the steps of:
    obtaining mycelia of an ectomycorrhizal fungus,
    contacting a propagule of said mycelia with a Fowells and Krauss's nutrient solution modified by the addition of glucose and thiamine and a particulate carrier, and
    maintaining said contact in the absence of living plant matter in darkness and without aeration for a period of time effective to stress the mycelia, inducing it to produce at least microsclerotia or its initials among said mycelia, and
    obtaining an ectomycorrhizal inoculum containing at least microsclerotia or the initials of microsclerotia, which inoculum is capable of producing intracellular hyphae when contacted with herbaceous plants.

15. A mycorrhizal inoculant for either woody or herbaceous plants produced from mycelia of at least one isolated and cultivated ectomycorrhizal fungi in the absence of living plant matter, said inoculant consisting essentially of said fungi and including at least microsclerotia or the initials of microsclerotia of said fungi, said inoculant being capable of producing intracellular hyphae when contacted with herbaceous plants which are effective to form endomycorrhizal symbiotic associations with herbaceous plants and producing mycorrhizal symbiotic associations with woody plants.

16. The inoculant of claim 15 wherein said mycelia of isolated ectomycrorrhizal fungi are selected from the group consisting of *Rizopogon roseolus, Pisolithus tinctorius, Amanita muscaria, Astraeus hygrometricus, Cenococcum geophilum, Scleroderma aurantium, Athelia neuhoffii, Boletinellus merulioides, Hebeloma anthracophilum, Hebeloma crustuliniforme, Paxillus involutus, Piloderma bicolor, Rhizopogon nigrescens, Scleroderma albidum, Scleroderma polyrhizum, Suillus cothurnatus, Alpova pachyploeus, Boletus punctipes,* and *Lactarius deliciosus.*

* * * * *